(12) United States Patent
Mochizuki et al.

(10) Patent No.: US 10,835,212 B2
(45) Date of Patent: Nov. 17, 2020

(54) MEDICAL IMAGE PROCESSING APPARATUS

(71) Applicant: TOSHIBA MEDICAL SYSTEMS CORPORATION, Otawara (JP)

(72) Inventors: Fumio Mochizuki, Kawasaki (JP);
Koichiro Kurita, Nasushiobara (JP);
Takeshi Fukasawa, Nasushiobara (JP);
Satoshi Matsunaga, Nasushiobara (JP);
Koji Kuroiwa, Fuchu (JP); Shogo Fukuda, Kawasaki (JP)

(73) Assignee: Canon Medical Systems Corporation, Otawara (JP)

( * ) Notice: Subject to any disclaimer, the term of this patent is extended or adjusted under 35 U.S.C. 154(b) by 810 days.

(21) Appl. No.: 15/449,432

(22) Filed: Mar. 3, 2017

(65) Prior Publication Data
US 2017/0281136 A1    Oct. 5, 2017

(30) Foreign Application Priority Data

Apr. 1, 2016  (JP) .................................. 2016-074539
Feb. 27, 2017 (JP) .................................. 2017-034521

(51) Int. Cl.
*A61B 8/00* (2006.01)
*A61B 8/08* (2006.01)
*A61B 8/14* (2006.01)

(52) U.S. Cl.
CPC .......... *A61B 8/5253* (2013.01); *A61B 8/0841* (2013.01); *A61B 8/14* (2013.01); *A61B 8/488* (2013.01); *A61B 8/5207* (2013.01); *A61B 8/5246* (2013.01)

(58) Field of Classification Search
None
See application file for complete search history.

(56) References Cited

U.S. PATENT DOCUMENTS

| | | | | |
|---|---|---|---|---|
| 2002/0173719 A1* | 11/2002 | Zhao | ................... | A61B 8/0833 600/437 |
| 2012/0078103 A1* | 3/2012 | Tashiro | ................ | A61B 8/0841 600/443 |
| 2014/0031673 A1* | 1/2014 | Amemiya | ............ | A61B 8/0841 600/424 |
| 2015/0141828 A1* | 5/2015 | Yoshiara | ................ | A61B 8/483 600/447 |
| 2015/0223776 A1* | 8/2015 | Ohuchi | ................ | A61B 8/0841 600/424 |

FOREIGN PATENT DOCUMENTS

JP    2014-23670    2/2014

* cited by examiner

*Primary Examiner* — Joel F Brutus
(74) *Attorney, Agent, or Firm* — Oblon, McClelland, Maier & Neustadt, L.L.P.

(57) ABSTRACT

According to one embodiment, an ultrasonic diagnostic apparatus includes a transmission/reception circuit and processing circuitry. The transmission/reception circuit performs a first scan and a second scan, which are different in acoustic field in an elevation direction, by controlling at least one of transducers arranged along an azimuth direction and the elevation direction. The processing circuitry generates a first needle-enhanced image by using data acquired in the first scan, and generates a second needle-enhanced image by using data acquired in the second scan.

19 Claims, 8 Drawing Sheets

MEDICAL IMAGE PROCESSING APPARATUS

CROSS-REFERENCE TO RELATED APPLICATIONS

This application claims the benefit of priority of Japanese Patent Application No. 2016-074539, filed Apr. 1, 2016, and Japanese Patent Application No. 2017-034521, filed Feb. 27, 2017, the entire contents of all of which are incorporated herein by reference.

FIELD

Embodiments described herein relate generally to an ultrasonic diagnostic apparatus and an ultrasonic image generation method.

BACKGROUND

Ultrasonic images imaged by an ultrasonic diagnostic apparatus are used for monitoring in paracentesis in some cases. In such cases, it is preferable to display both of a B-mode image and a needle-enhanced image in which a puncture needle is emphasized, because the B-mode image is effective for confirming a body tissue and the needle-enhanced image is effective for confirming a position of the puncture needle.

As a method of generating a needle-enhanced image, there is a known method of performing a scan for generating a needle-enhanced image (hereinafter, referred to as a needle-enhanced scan) aside from a scan for generating a body-tissue image (hereinafter, referred to as a body-tissue scan) and displaying a composite image of a needle-enhanced image and a body-tissue image such as a B-mode image. However, when a puncture needle is displaced from an acoustic field (hereinafter, such a state is referred to as an off-plane state), each echo signal from the puncture needle is weakened and visibility of the puncture needle is reduced.

As a technique of improving visibility of a puncture needle in such a type of off-plane state, there is a technique of widening width of an acoustic field in the elevation direction in a needle-enhanced scan more than that in a body-tissue scan by using an ultrasonic probe in which plural ultrasonic transducers are arranged in the elevation direction. According to this kind of technique, even if a puncture needle is in the off-plane state with respect to an acoustic field of a body-tissue scan, an ultrasonic probe can receive echo signals of strong intensity from this puncture needle when the puncture needle is positioned within an acoustic field of a needle-enhanced scan.

However, when width of an acoustic field of a needle-enhanced scan in the elevation direction is widened, a reception beam does not sufficiently converge, which blurs a puncture needle depicted in a needle-enhanced image. Further, in this case, a B-mode image and a needle-enhanced image have different imaging region. Thus, when a composite image of a body-tissue image and a needle-enhanced image are generated and displayed, it will be difficult for a user to recognize the actual position of the puncture needle spatially separated from the biological cross-section of the body-tissue image, which may sometimes impair the safety and reliability of medical treatment.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of an ultrasonic diagnostic apparatus and an ultrasonic image generation method according to embodiments of the present invention with reference to the drawings. An ultrasonic diagnostic apparatus according to one embodiment of the present invention may be used when paracentesis is performed under guidance of ultrasonic images for example.

In general, according to one embodiment, an ultrasonic diagnostic apparatus includes a transmission/reception circuit and processing circuitry. The transmission/reception circuit performs a first scan and a second scan, which are different in acoustic field in an elevation direction, by controlling at least one of transducers arranged along an azimuth direction and the elevation direction. The processing circuitry generates a first needle-enhanced image by using data acquired in the first scan, and generates a second needle-enhanced image by using data acquired in the second scan.

Figure 1:
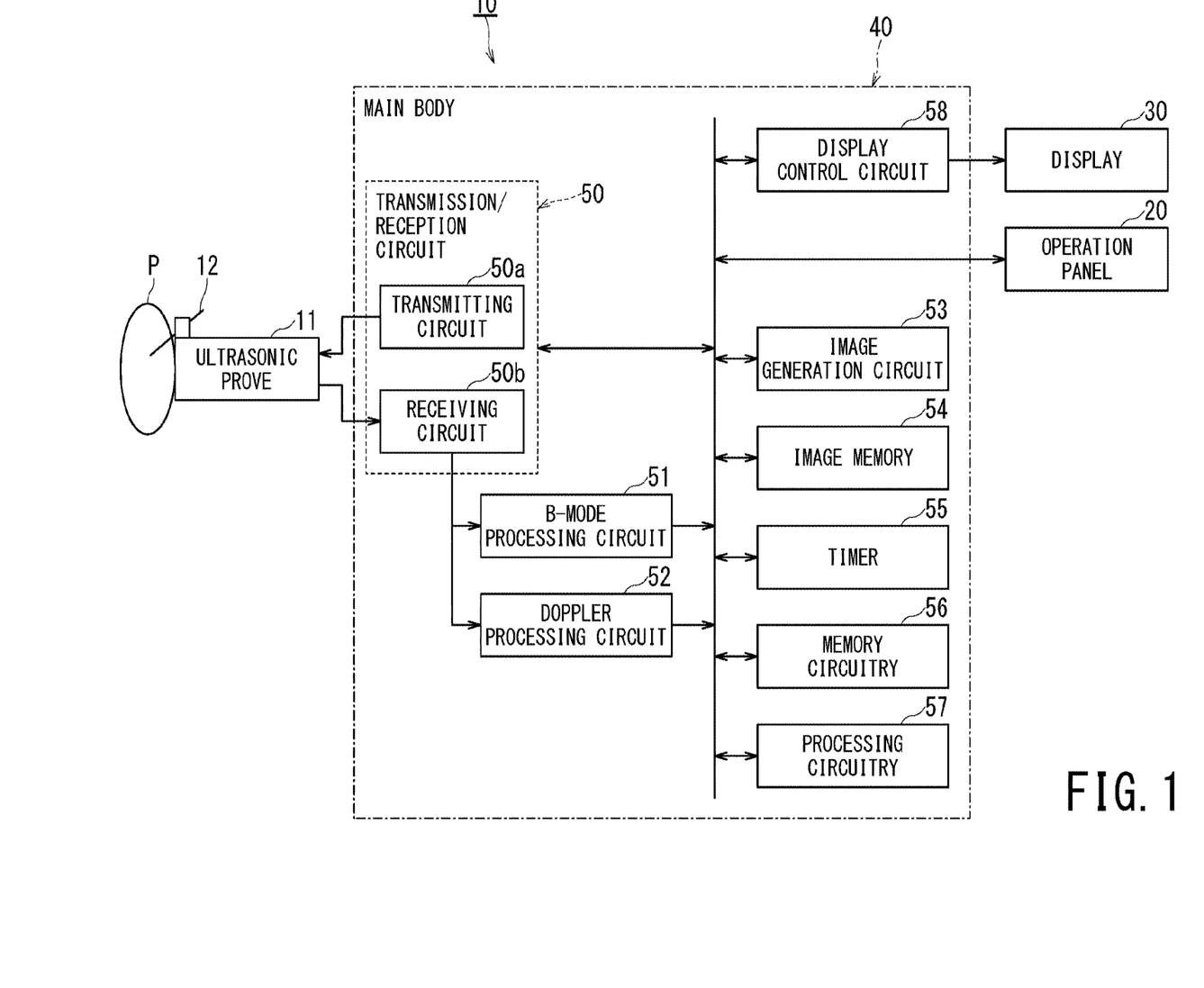
FIG. 1 is a block diagram illustrating a configuration of the ultrasonic diagnostic apparatus according to the first embodiment of the present invention.

FIG. 1 is a block diagram illustrating a configuration of the ultrasonic diagnostic apparatus 10 of the present embodiment. The ultrasonic diagnostic apparatus 10 includes an ultrasonic probe 11, a puncture needle 12, an operation panel 20, a display 30, and a main body 40.

Figure 2:
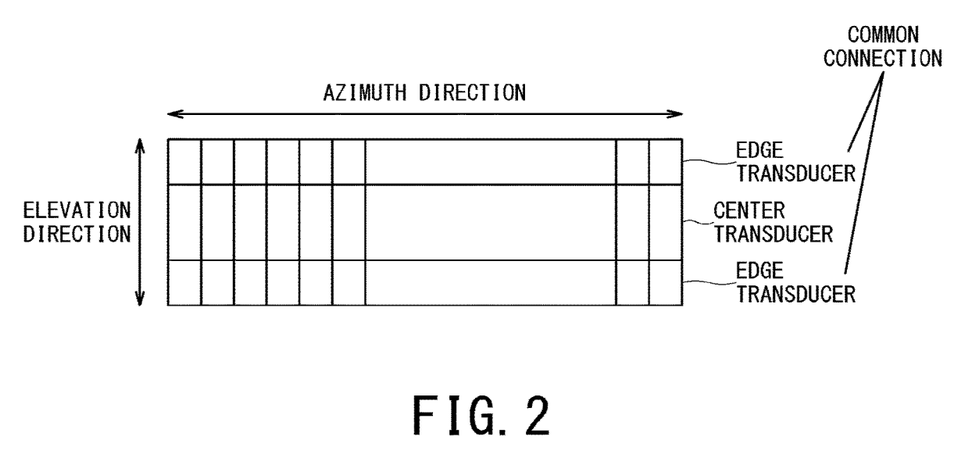
FIG. 2 is a schematic plan view illustrating arrangement of ultrasonic transducers constituting an ultrasonic probe.

FIG. 2 is a schematic plan view illustrating arrangement of ultrasonic transducers constituting the ultrasonic probe 11. The ultrasonic probe 11 is equipped with plural ultrasonic transducers (piezoelectric vibrators). Each of those plural ultrasonic transducers generates an ultrasonic wave based on a drive signal supplied from the main body 40. The ultrasonic probe 11 transmits ultrasonic waves generated by the ultrasonic transducers to inside of a body of an object P, and receives echo signals from the object P so as to convert the echo signals into electric signals. Moreover, the ultrasonic probe 11 includes components such as a matching layer provided on the ultrasonic transducers and a backing material which prevents ultrasonic waves from propagating toward the back side of the ultrasonic transducers.

In the present embodiment, the ultrasonic probe 11 is configured to be able to perform the first and second scans which are different in acoustic field in the elevation direction (also referred to as the slice direction) from each other. Thus, a two-dimensional array probe in which plural transducers are arranged in the elevation direction can be used as the ultrasonic probe 11. As such a type of two-dimensional array probe, a 1.5-dimensional array probe, a 1.75-dimensional array probe, and a two-dimensional array probe can be used for example.

The above-described 1.5-dimensional array probe is such a probe that transducers equidistant from the center in the elevation direction are connected with each other (FIG. 2), an acoustic field of an ultrasonic wave is symmetric along the elevation direction about the center axis, and delay of transmitted/received ultrasonic waves and apodization can be controlled so as to be symmetric about the center axis in the elevation direction.

The above-described 1.75-dimensional array probe is such a probe that its aperture is variable in the elevation direction, its focal length can be dynamically changed, and an acoustic field of an ultrasonic wave in the elevation direction can be asymmetric about the center axis.

The above-described two-dimensional array probe is such a probe that transmission/reception signal lines of respective transducers are independent of each other, and delay of transmitted/received ultrasonic waves, apodization, the acoustic field center, and a transmission/reception angle can be controlled in the elevation direction. In the following, a case where a 1.5-dimensional array probe is used as the ultrasonic probe 11 will be described.

The puncture needle 12 is mounted on the ultrasonic probe 11 via a guide attachment or the like, and is punctured into a predetermined part of the object P by a user.

The operation panel 20 functions as a touch command screen, and includes a display, a touch input circuit disposed beside this display, and a hardware key 22. The touch input circuit provides the main body 40 with information on an instruction position on a touch input circuit touched by a user. A keyboard, a mouse, a foot switch, a track ball, various types of buttons and the like can be used as the hardware key 22. The touch input circuit and the hardware key integrally constitute an input circuit which receives various types of commands from a user of the ultrasonic diagnostic apparatus 10.

The display 30 is configured of a general display output device such as a liquid crystal display and an OLED (Organic Light Emitting Diode) display, and display an ultrasonic image such as a composite image of a body-tissue image and a puncture support image generated by the main body 40. Additionally, the display 30 displays an image for a user of the ultrasonic diagnostic apparatus 10 to input various types of commands with the use of the operation panel 20. Further, the display 30 displays notification information for a user received from the main body 40.

The main body 40 generates an ultrasonic image based on an echo signal from the object P received by the ultrasonic probe 11. As shown in FIG. 1, the main body 40 includes a transmission/reception circuit 50, a B-mode processing circuit 51, a Doppler processing circuit 52, an image generation circuit 53, an image memory 54, a timer 55, memory circuitry 56, processing circuitry 57, and a display control circuit 58.

The transmission/reception circuit 50 includes a transmitting circuit 50a and a receiving circuit 50b, and controls transmission directivity and reception directivity in transmission and reception of ultrasonic waves in cooperation with the processing circuitry 57. Although a description has been given of a case where the transmission/reception circuit 50 is provided on the main body 40 in FIG. 1, the transmission/reception circuit 50 may be provided on the ultrasonic probe 11 or may be provide on both the ultrasonic probe 11 and the main body 40.

The transmitting circuit 50a includes a pulse generator, a transmission delay circuit, and a pulsar circuit, and supplies the ultrasonic probe 11 with a driving signal. The pulse generator repeatedly generates a rate pulse for forming an ultrasonic wave to be transmitted at a predetermined rate frequency. The transmission delay circuit diffuses or focuses an ultrasonic wave generated from the ultrasonic probe 11 into a beam and provides, to each rate pulse generated by the pulse generator, a delay time per ultrasonic transducer that is necessary to determine the transmission directionality. Additionally, the pulsar circuit applies a driving pulse to the ultrasonic probe 11 at a timing based on each rate pulse. The transmission delay circuit changes the delay time provided to each rate pulse so as to appropriately adjust a transmission direction of an ultrasonic wave in which the ultrasonic waves transmitted from the surface of the ultrasonic transducers is transmitted.

Further, in order to execute a predetermined scan sequence under the control of the processing circuitry 57, the transmitting circuit 50a has a function of instantaneously changing parameters such as a transmission frequency and a transmission driving voltage. The function of changing a transmission driving voltage is implemented by a linear amplifier type of oscillator capable of instantaneously changing the value of the transmission driving voltage or a structure of electrically switching plural power-supply units.

The receiving circuit 50b includes an amplifier circuit, an A/D converter, and an adder circuit. The receiving circuit 50b receives echo signals received by the ultrasonic probe 11 and generates reflected wave data by performing various types of processing on the echo signals. The amplifier circuit performs gain correction processing by amplifying the echo signals for each channel. The A/D converter performs A/D conversion on the reflected wave signals subjected to the gain correction processing, and provides the digitized data with a delay time necessary for determining reception directivity. The adder circuit performs addition processing of the echo signals digitized by the A/D converter so as to generate reflected wave data. Each reflected component from a direction according to reception directivity of each echo signal is enhanced by the addition processing of the adder circuit.

The B-mode processing circuit 51 receives reflected wave data from the receiving circuit 50b and performs logarithmic amplification, envelope detection on the reflected wave data, and the like, so as to generate (B-mode) data expressing the signal intensity by luminance brightness.

The Doppler processing circuit 52 performs frequency analysis on velocity information from the reflected wave data received from the receiving circuit 50b, and extracts a blood-flow component, a tissue component, and a contrast-agent echo component by the Doppler effect. In this manner, the Doppler processing circuit 52 generates Doppler data in which moving-object information items such as the average velocity, variance, and power are extracted for multiple points.

The image generation circuit 53 generates an ultrasonic image based on reflected waves received by the ultrasonic probe 11. Specifically, the image generation circuit 53 generates an ultrasonic image from data generated by the B-mode processing circuit 51 and the Doppler processing circuit 52. For instance, the image generation circuit 53 generates a B-mode image in which intensity of each reflected wave is indicated by brightness based on two-dimensional B-mode data generated by the B-mode processing circuit 51.

Additionally, the image generation circuit 53 generates a color Doppler image indicative of moving-object information from two-dimensional Doppler data generated by the Doppler processing circuit 52. Such a color Doppler image is generated as an average velocity image, a variance image, a power image, or a combination image of these images. In the following description, an ultrasonic image such as a two-dimensional B-mode image and a two-dimensional color Doppler image is arbitrarily referred to as a body-tissue image.

In general, the image generation circuit 53 converts signal lines of respective ultrasonic scanlines into scanning signal lines of a video format typified by a television format so as to generate a two-dimensional ultrasonic image for display. Specifically, the image generation circuit 53 generates a two-dimensional ultrasonic image to be displayed by performing coordinate conversion according to the mode of scanning using ultrasound performed by the ultrasonic probe 11.

The image memory 54 is a memory circuit configured to store data of ultrasonic images generated by the image generation circuit 53 such as a B-mode image and a color Doppler image.

The timer 55 is controlled by the processing circuitry 57, and is activated by setting a predetermined time. For instance, assuming that a threshold value Tth is set to the timer 55 and the timer 55 is activated so as to start time-count, the timer 55 outputs a time-out signal and stops time-count when the timer threshold value Tth elapses after the start of time-count.

The memory circuitry 56 is equipped with a configuration including memory media which can be read by a processor such as a magnetic memory medium, an optical memory medium, and a semiconductor memory. The memory circuitry 56 may be configured such that some or all of the programs and data stored in those memory media can be downloaded by means of communication via an electronic network.

The processing circuitry 57 is a processor configured, by executing programs, to execute processing for a user to easily understand positional relationship between the puncture needle 12 and a biological cross-section corresponding to a body-tissue image.

The display control circuit 58 includes a GPU (Graphics Processing Unit) and a VRAM (Video Random Access Memory). The display control circuit 58 causes the display 30 to display an image which is requested to be displayed by the processing circuitry 57, under the control of the processing circuitry 57. The display control circuit 58 may display an image, which is substantially equivalent to the image displayed on the display 30, on the display of the operation panel 20.

Figure 3:
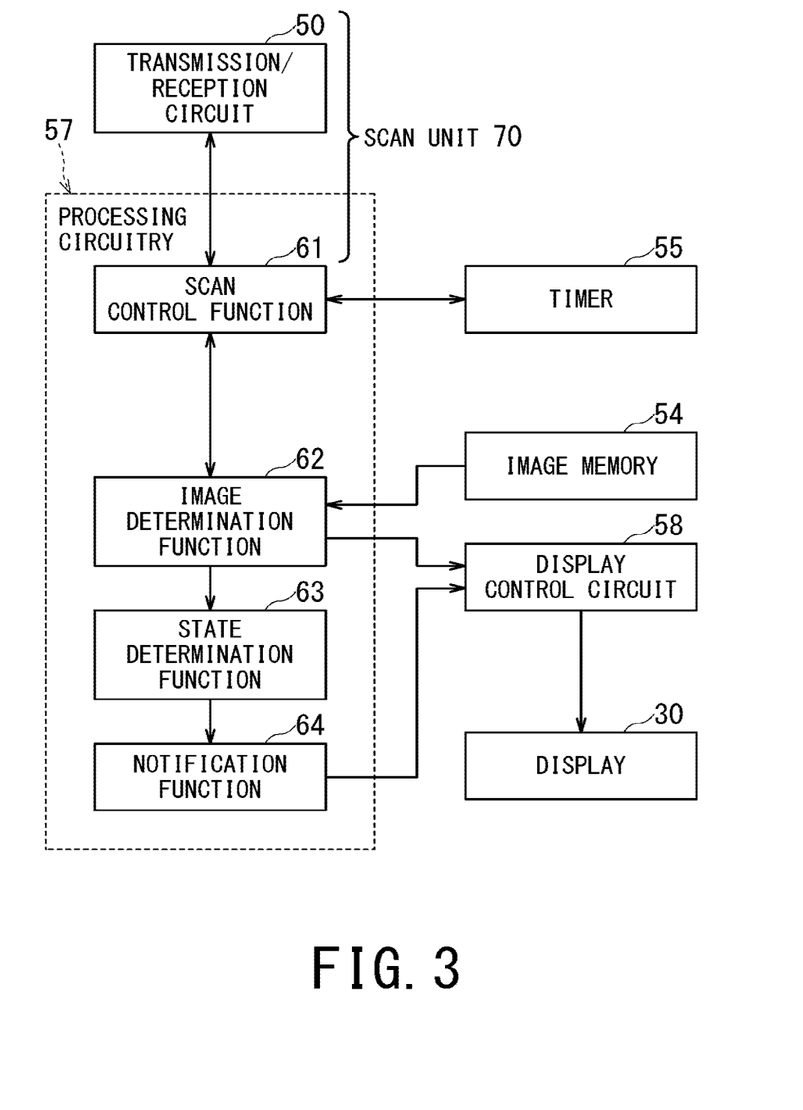
FIG. 3 is a general block diagram illustrating functions implemented by a processor of processing circuitry.

FIG. 3 is a general block diagram illustrating functions implemented by the processor of the processing circuitry 57.

As shown in FIG. 3, the processor of the processing circuitry 57 implements a scan control function 61, an image generation function 62, a state determination function 63, and a notification function 64. The respective functions 61 to 64 are stored in the form of programs in the memory circuitry 56.

First, outlines of functions 61 to 64 will be described.

The scan control function 61 and the transmission/reception circuit 50 integrally constitute a scan unit 70. The scan unit 70 performs the first and second scans being different in acoustic field in the elevation direction from each other, by controlling at least one of the plural ultrasonic transducers of the ultrasonic probe 11 arranged along the azimuth direction and the elevation direction. The scan control function 61 controls the transmission/reception circuit 50 so as to cause the transmission/reception circuit 50 to perform the first and second scans which are different in acoustic field in the elevation direction from each other.

The image generation function 62 generates the first needle-enhanced image from ultrasonic data acquired in the first scan, and generates the second needle-enhanced image from ultrasonic data acquired in the second scan. Additionally, the image generation function 62 generates a puncture support image as puncture support information by composing the first needle-enhanced image with the second needle-enhanced image. Further, the image generation function 62 generates a body-tissue image from ultrasonic data acquired in a body-tissue scan, and generates a composite image of this body-tissue image and the puncture support image so as to cause the display 30 to display the composite image.

Moreover, the image generation function 62 may have a mode in which one of the first needle-enhanced image and the second needle-enhanced image is displayed on the display 30 (hereinafter, referred to as a switching mode). In the switching mode, an image to be displayed on the display 30 may be switched from one of the first and second needle-enhanced images to the other in an automatic manner according to setting of the ultrasonic diagnostic apparatus 10 or in a manual manner according to an instruction from a user.

The state determination function 63 determines whether the puncture needle 12 is displaced from an acoustic field of a body-tissue scan or not (i.e., whether it is in the off-plane state or not). For instance, the state determination function 63 determines to be in the off-plane state when a predetermined ratio is not lower than a ratio obtained by dividing the number of pixels of the first needle-enhanced image whose pixel values are equal to or higher than a predetermined pixel value by the number of pixels of the second needle-enhanced image whose pixel values are equal to or higher than a predetermined pixel value.

When the state determination function 63 determines that it is in the off-plane state, the notification function 64 outputs puncture support information indicating that it is in the off-plane state. Specifically, when the state determination function 63 determines to be in the off-plane state, the notification function 64 notifies a user of being in the off-plane state by causing the display 30 to display an image indicative of being in the off-plane state or causing a non-illustrated speaker to output sound such as voice or a beep indicative of the same.

Plural scans being different in acoustic field in the elevation direction from each other are performed for generating the puncture support image, and plural scans can be three or more scans.

In the following, a description will be given of a case where two scans, i.e., the first scan and the second scan, are performed for generating the puncture support image. Additionally, out of the first scan and the second scan, the one which is narrower in width of an acoustic field in the elevation direction is referred to as a narrow-field needle-enhanced scan, and the other is referred to as a wide-field needle-enhanced scan.

Next, details of the respective functions 61 to 64 will be described with reference to FIG. 4 to FIG. 8.

Figure 4:
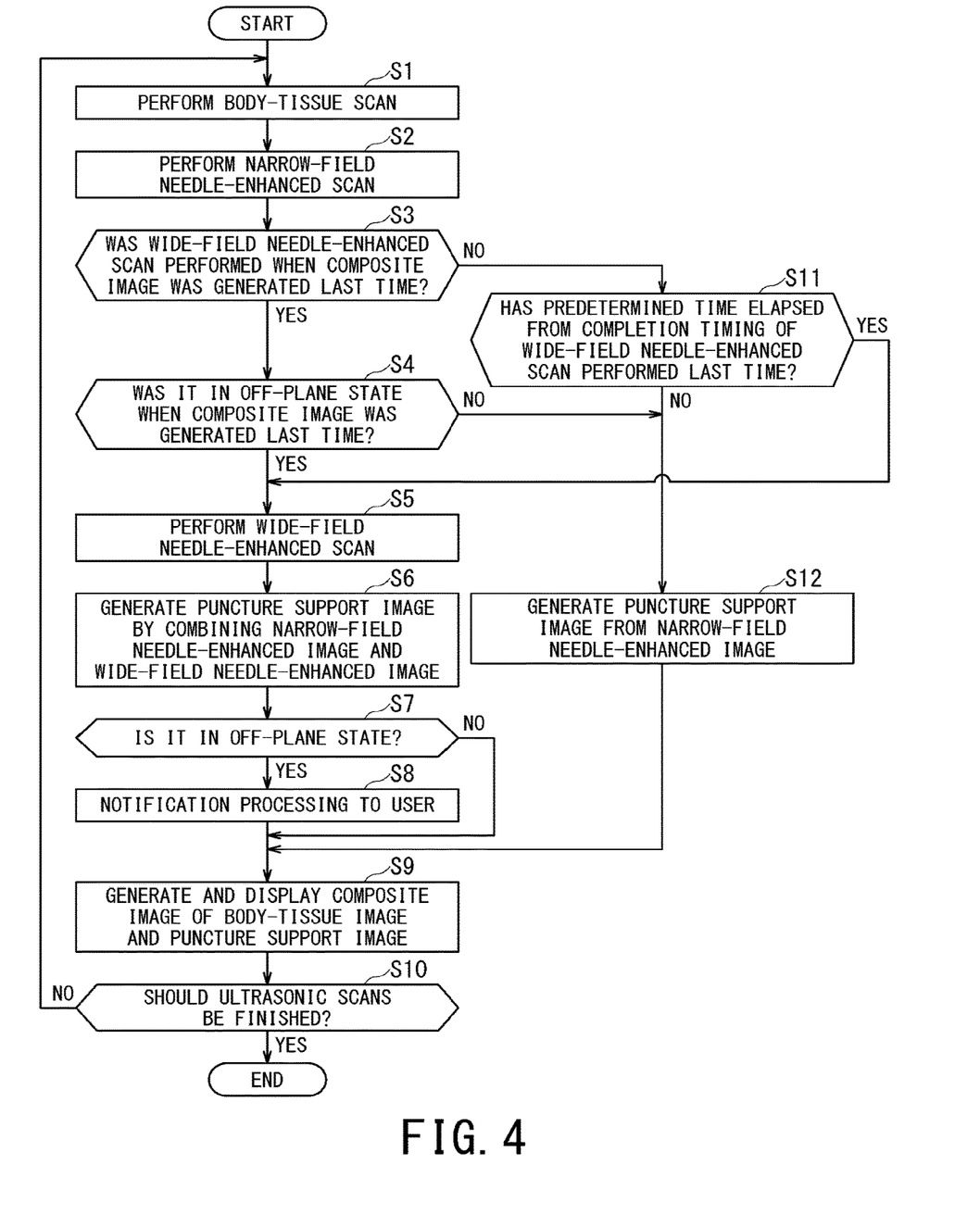
FIG. 4 is a flowchart illustrating processing performed by the processor of the processing circuitry in order to assist a user in easily understanding positional relationship between a puncture needle and a biological cross-section corresponding to a body-tissue image.

FIG. 4 is a flowchart illustrating processing performed by the processor of the processing circuitry 57 in order to assist a user in easily understanding positional relationship between the puncture needle 12 and a biological cross-section corresponding to a body-tissue image. In FIG. 4, each reference sign composed of S and number on its right side indicates step number of the flowchart.

Further, in FIG. 4, a description will be given of a case where the narrow acoustic field 81 is equal to an acoustic field of a body-tissue scan, i.e., the narrow acoustic field 81 is equal to a biological cross-section corresponding to a body-tissue image.

First, in the step S1, the scan unit 70 sets width of an acoustic field in the elevation direction to predetermined width, and then performs a body-tissue scan. The image generation function 62 generates a body-tissue image based on an echo signal acquired by the body-tissue scan. It is preferable that the predetermined width of an acoustic field used in the body-tissue scan has a value corresponding to a sufficiently focused ultrasonic beam in order to make a body-tissue image as clearly as possible.

Next, in the step S2, the scan unit 70 performs a narrow-field needle-enhanced scan. Then, the image generation function 62 generates a narrow-field needle-enhanced image based on an echo signal acquired by the narrow-field needle-enhanced scan. It is preferable that width of an acoustic field in the elevation direction used in the narrow-field needle-enhanced scan is substantially the same as the above-described predetermined width of an acoustic field used in the body-tissue scan.

Here, a method of generating a puncture support image in the off-plane state will be described.

Figure 5A:
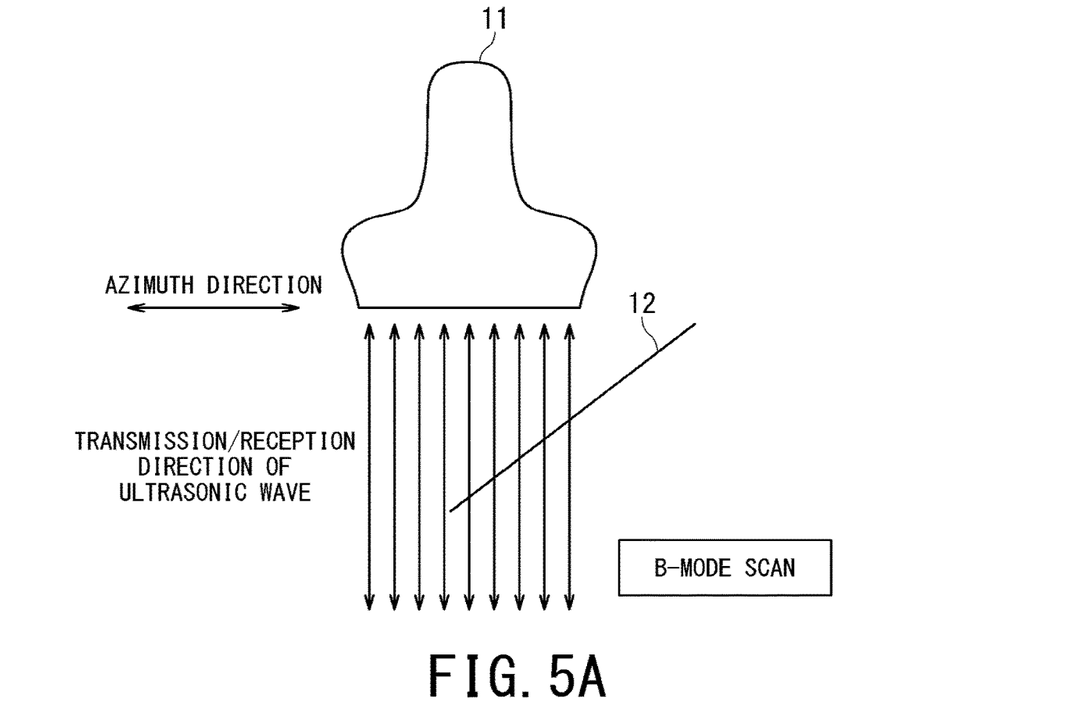
FIG. 5A is a schematic diagram illustrating a position of a puncture needle in relation to a transmission/reception direction of ultrasonic waves in a B-mode scan.
Figure 5B:
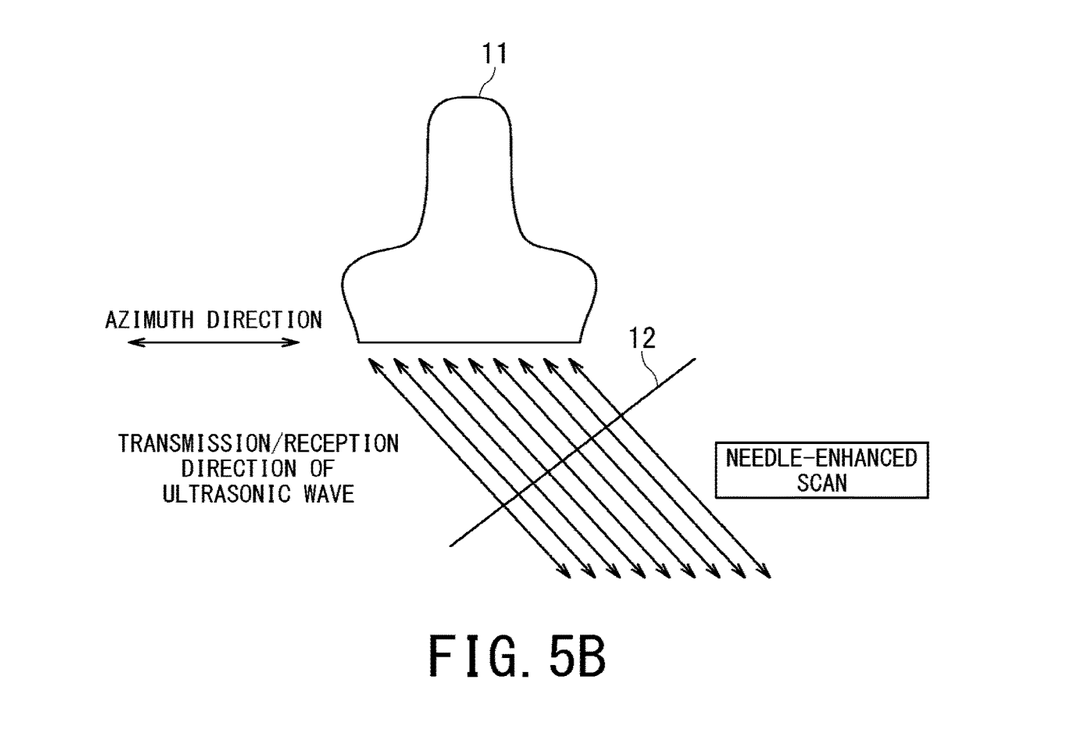
FIG. 5B is a schematic diagram illustrating a position of the puncture needle in relation to the transmission/reception direction of ultrasonic waves in a needle-enhanced scan.

FIG. 5A is a schematic diagram illustrating a position of the puncture needle 12 in relation to a transmission/reception direction of ultrasonic waves in the B-mode scan. FIG. 5B is a schematic diagram illustrating a position of the puncture needle 12 in relation to a transmission/reception direction of ultrasonic waves in the needle-enhanced scan. The term "needle-enhanced scan" is assumed to be a collective term of scans performed for generating a puncture support image such as the first scan and the second scan. Additionally, each of FIG. 5A and FIG. 5B illustrates a case where the ultrasonic probe 11 is a linear type.

The puncture needle 12 is not necessarily vertically punctured with respect to a body surface of the object P. Thus, as shown in FIG. 5A, in the B-mode scan as an example of a body-tissue scan, the puncture needle 12 is not perpendicular to the transmission/reception direction of ultrasonic waves in many cases. For this reason, in a needle-enhanced scan, the ultrasonic probe 11 transmits and receives ultrasonic waves in the direction perpendicular to the puncture needle 12 such that stronger echo signals of the puncture needle 12 can be received (FIG. 5B). An image in which only the puncture needle 12 is extracted can be acquired by performing predetermined processing such as gain adjustment on echo signals acquired in the needle-enhanced scan.

As to the narrow-field needle-enhanced image and the wide-field needle-enhanced image, images of corresponding plural steering angles (e.g., three angles of 15°, 30°, and) 45° may be acquired and one of these images in which the echo signal from the puncture needle 12 is the strongest may be used as the narrow-field needle-enhanced image and a wide-field needle-enhanced image. Additionally, the needle extraction processing is not limited to the aforementioned gain adjustment. For instance, time-sequential images may be acquired at the certain steering angle in each acoustic field of the narrow-field needle-enhanced scan and the wide-field needle-enhanced scan, and the puncture needle 12 in motion may be extracted based on motion vector between these time-sequential images.

Figure 6A:
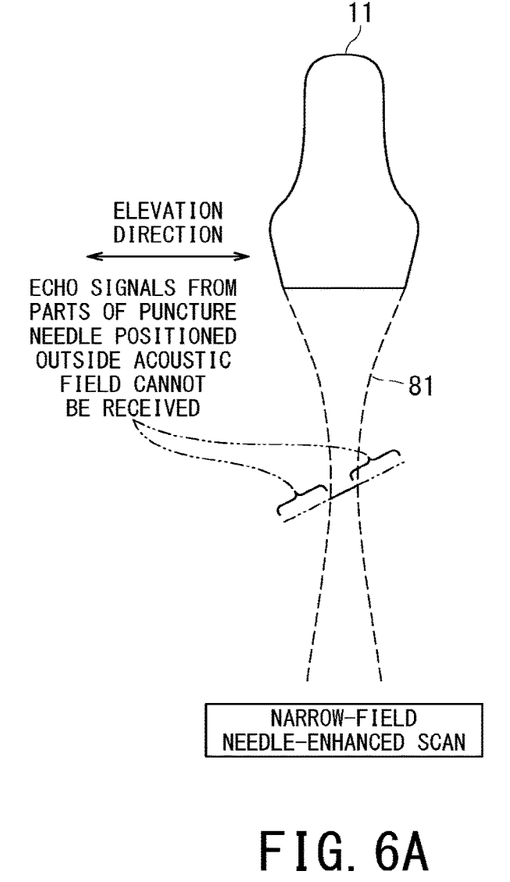
FIG. 6A is a schematic diagram illustrating a narrow acoustic field in a narrow-field needle-enhanced scan.
Figure 6B:
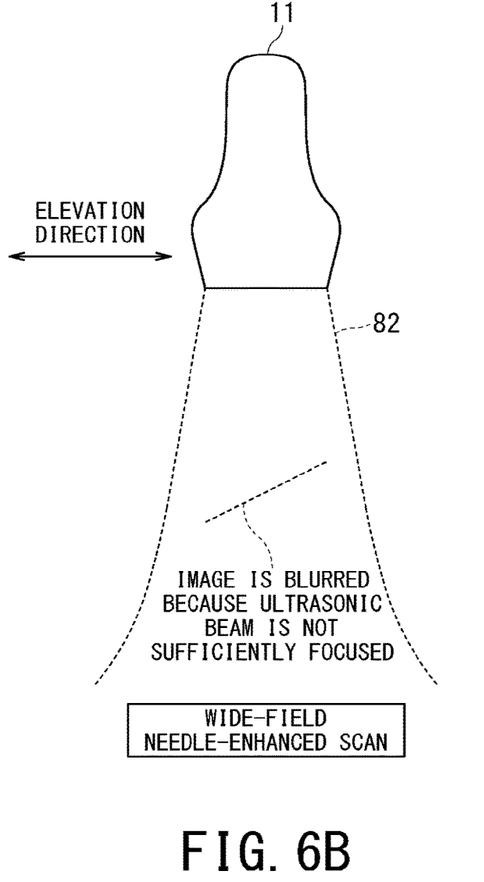
FIG. 6B is a schematic diagram illustrating a wide acoustic field in a wide-field needle-enhanced scan.

FIG. 6A is a schematic diagram illustrating the narrow acoustic field 81 in the narrow-field needle-enhanced scan, and FIG. 6B is a schematic diagram illustrating the wide acoustic field 82 in the wide-field needle-enhanced scan.

Since an ultrasonic beam is sufficiently focused in the narrow-field needle-enhanced scan, a part of the puncture needle 12 positioned within the narrow acoustic field 81 is clearly depicted in the acquired image (as shown by the solid line in FIG. 6A), while echo signal cannot be received from a part of the puncture needle 12 positioned outside the narrow acoustic field 81 (as shown by the two-dot chain line in FIG. 6A).

In the wide-field needle-enhanced scan, though an echo signal can be received from any part of the puncture needle 12 positioned within the wide acoustic field 82, the image of the puncture needle 12 is blurred because the ultrasonic beam is not sufficiently focused (as shown by the broken line in FIG. 6B). Incidentally, it is enough that the wide acoustic field 82 is wider in the elevation direction than the narrow acoustic field 81, the wide acoustic field 82 includes not only an acoustic field formed by narrowing effective (radiation) range of an ultrasonic beam compared with the narrow acoustic field 81 but also an acoustic field formed by diffusing an ultrasonic beam.

Figure 7:
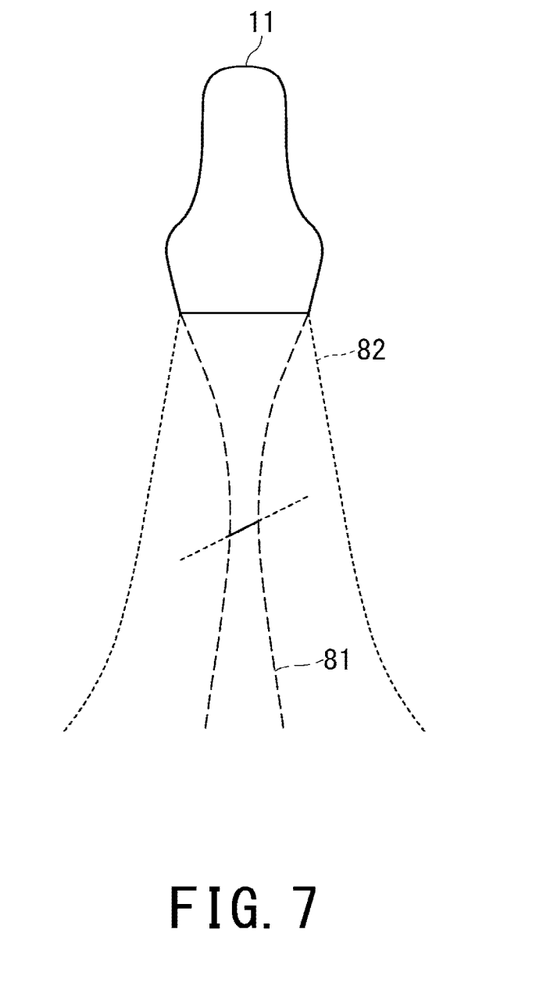
FIG. 7 is a schematic diagram illustrating relationship between a puncture support image generated by combining a narrow-field needle-enhanced image with a wide-field needle-enhanced image in the off-plane state, a narrow acoustic field, and a wide acoustic field.

FIG. 7 is a schematic diagram illustrating relationship between a puncture support image generated by combining a narrow-field needle-enhanced image with a wide-field needle-enhanced image in the off-plane state, the narrow acoustic field 81, and the wide acoustic field 82.

Since the part of the puncture needle 12 depicted in the narrow-field needle-enhanced image is too small in the off-plane state, it is difficult for a user to recognize the position of the puncture needle 12 only from the narrow-field needle-enhanced image. For this reason, the image generation function 62 of the present embodiment generates a puncture support image by combining the narrow-field needle-enhanced image and the wide-field needle-enhanced image in the off-plane state.

Returning to FIG. 4, after generating the narrow-field needle-enhanced image by performing the narrow-field needle-enhanced scan in the step S2, in the step S3, the scan control function 61 determines whether or not the wide-field needle-enhanced scan was performed in the last executed procedure (the steps S1 to S12).

When the wide-field needle-enhanced scan was performed in the last executed procedure (YES in step S3), and it was in the off-plane state in the last executed procedure (YES in step S4), then the processing proceeds to the step 5. In the step S5, the scan control function 61 performs the wide-field needle-enhanced scan, and the image generation function 62 generates a wide-field needle-enhanced image based on data acquired in this wide-field needle-enhanced scan. Additionally, when performing the wide-field needle-enhanced scan, the scan control function 61 sets the timer threshold value Tth so as to activate the timer 55 and cause the timer 55 to start time-count. When the timer 55 has already been activated and is executing time-count, the scan control function 61 resets the timer 55 and sets the timer threshold value Tth again so as to cause the timer 55 to restart time-count. The time-count information of the timer 55 is used in the subsequent procedures to be executed after returning to the step S1 from the step S10.

In the next step S6, the image generation function 62 generates a puncture support image by combining the narrow-field needle-enhanced image and the wide-field needle-enhanced image. In this image-composition processing, the image generation function 62 generates the puncture support image by prioritizing the narrow-field needle-enhanced image over the wide-field needle-enhanced image.

In the next step S7, the state determination function 63 determines whether or not the puncture needle 12 is displaced from the narrow acoustic field 81 being also an acoustic field of the body-tissue scan, i.e., whether or not it is in the off-plane state. Specifically, the state determination function 63 determines to be in the off-plane state when the ratio, which is obtained by dividing the number of pixels of the narrow-field needle-enhanced image whose pixel values are not less than a predetermined pixel value by the number of pixels of the wide-field needle-enhanced image whose pixel values are not less than a predetermined pixel value, is lower than a predetermined ratio. The above-described predetermined pixel value may preferably be a pixel value whereby echo signals from body tissues can be eliminated and echo signals from the puncture needle 12 can be extracted. Additionally, as the above-described predetermined ratio, a value within the range of 80% to 100% may preferably be used. The state determination function 63 stores the information of the determination result of the step S7 in the memory circuitry 56 for example. When the state determination function 63 determines that it is in the off-plane state, the processing proceeds to the step S8. Conversely, when the state determination function 63 determines that it is not in the off-plane state, the processing proceeds to the step S9.

In the next step S8, the notification function 64 informs a user of being in the off-plane state by causing the display 30 to display information indicative of being in the off-plane state, causing a non-illustrated speaker to output voice indicative of being in the off-plane state, or causing both of the display 30 and speaker to output such information, or the like. Additionally, when the ultrasonic probe 11 is a two-dimensional array probe, the state determination function 63 can recognize the position of the puncture needle 12 with respect to the narrow acoustic field 81. In order to resolve the off-plane state in this case, the notification function 64 may preferably cause the display 30 to display information on the translational direction and the rotational direction in which the ultrasonic probe 11 should be moved, cause the speaker to output voice indicating the same information, or execute both of them.

Figure 8:
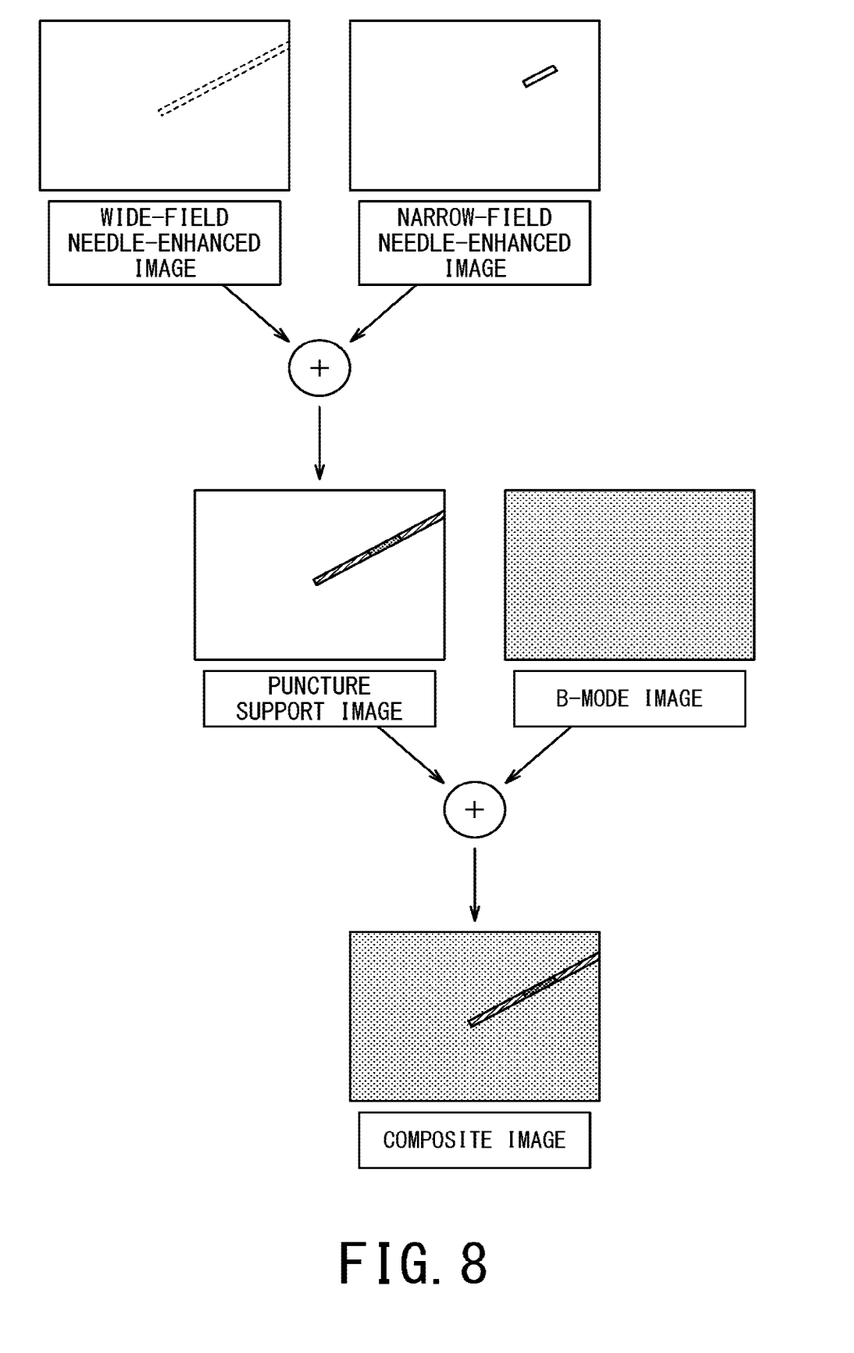
FIG. 8 is a schematic diagram illustrating a puncture support image and a composite image.

FIG. 8 is a schematic diagram illustrating a puncture support image and a composite image. In FIG. 8, a case where a B-mode image is used as a body-tissue image is illustrated.

In the next step S9, the image generation function 62 generates a composite image by combining the body-tissue image and the puncture support image, and causes the display 30 to display the composite image (the bottom part of FIG. 8).

As shown in FIG. 7, the puncture needle 12 is sharply depicted in the narrow-field needle-enhanced image, while being blurred and unclearly depicted in the wide-field needle-enhanced image. Accordingly, a user can easily recognize positional relationship between the puncture needle 12 and acoustic fields including the narrow acoustic field 81 and the wide acoustic field 82 by confirming the puncture support image generated by combining the narrow-field needle-enhanced image and the wide-field needle-enhanced image.

Thus, a user can easily position the puncture needle 12 within the narrow acoustic field 81 thereby resolving the off-plane state by rotating the ultrasonic probe 11 such that the ratio of the wide-field needle-enhanced image is reduced while watching the puncture support image. Further, a user can obtain a clear image of the puncture needle 12 in paracentesis by resolving the off-plane state. Since a user can pierce the puncture needle 12 within a biological cross-section of the body-tissue image by resolving the off-plane state, safety and reliability of medical treatment can be greatly improved.

Further, as shown in the left of the middle part of FIG. 8, the image generation function 62 may preferably generate the puncture support image such that the part of the puncture needle 12 included in the wide-field needle-enhanced image and the rest of the puncture needle 12 included in the narrow-field needle-enhanced image are different in display mode. For instance, in the puncture support image, the part of the puncture needle 12 included in the narrow-field needle-enhanced image may be indicated by a dotted area, while the rest of the puncture needle 12 included in the wide-field needle-enhanced image may be indicated by a hatched area.

In this case where the part of the puncture needle 12 included in the wide-field needle-enhanced image and the rest of the puncture needle 12 included in the narrow-field needle-enhanced image are displayed together in the puncture support image in display modes different from each other, a user can more easily recognize positional relationship between the puncture needle 12 and acoustic fields including the narrow acoustic field 81 and the wide acoustic field 82 by confirming the display mode of the puncture needle 12. Accordingly, in this case, a user can easily recognize positional relationship between the puncture needle 12 and the biological cross-section corresponding to the body-tissue image by confirming the puncture support image.

Specifically, the image generation function 62 may preferably determine pixel values of respective pixels of the narrow-field needle-enhanced image by using the same color map as the body-tissue image (e.g., a color map in which color to be assigned to a pixel gradually changes from black to white in gray scale as a luminance value of the pixel increases). Further, the image generation function 62 may preferably determine pixel values of respective pixels of the wide-field needle-enhanced image by using a color map different from the color map for the narrow-field needle-enhanced image (e.g., a color map in which color to be assigned to the pixel gradually changes from blue to red in chromatic color as a luminance value of the pixel increases). In this case, the higher the ratio of the wide-field needle-enhanced image combined in the puncture support image is (i.e., the more the puncture needle 12 is displaced from the narrow acoustic field 81), the higher the ratio of chromatic color in the puncture needle 12 becomes. By assigning color to the pixels as described above, a user can more easily recognize positional relationship between the puncture needle 12 and acoustic fields including the narrow acoustic field 81 and the wide acoustic field 82. The image generation function 62 may cause the display 30 to further display information indicating each meaning of color maps for the narrow-field needle-enhanced image and the wide-field needle-enhanced image.

Next, methods of generating the puncture support image implemented by the image generation function 62 in the step S6 will be described in more detail.

In the first method for generating the puncture support image such that the narrow-field needle-enhanced image is given priority over the wide-field needle-enhanced image, for each pixel a luminance value of the narrow-field needle-enhanced image and that of the wide-field needle-enhanced image are compared, and the larger luminance value is used as a luminance value of corresponding pixel of the puncture support image.

The puncture needle 12 depicted in the narrow-field needle-enhanced image is more in focus than the puncture needle 12 depicted in the wide-field needle-enhanced image. Accordingly, luminance values of respective pixels corresponding to the puncture needle 12 of the narrow-field needle-enhanced image are considered to be generally higher than luminance values of respective pixels corresponding to the puncture needle 12 of the wide-field needle-enhanced image. Thus, the puncture support image can be generated by the first method in such a manner that the narrow-field needle-enhanced image is given priority over the wide-field needle-enhanced image.

In the second method, luminance values of at least one of the narrow-field needle-enhanced image and the wide-field needle-enhanced image are weighted, whereby the narrow-field needle-enhanced image is given priority over the wide-field needle-enhanced image. The second method can be used in combination with the first method. Specifically, the narrow-field needle-enhanced image can be more surely given priority by performing comparison of luminance values for each pixel between both images after weighting is performed on pixel values in such a manner that the narrow-field needle-enhanced image is more emphasized than the wide-field needle-enhanced image.

In the third method, higher transparence degree is assigned to the wide-field needle-enhanced image than to the narrow-field needle-enhanced image, whereby the narrow-field needle-enhanced image is given priority over the wide-field needle-enhanced image in the puncture support image. Since the narrow-field needle-enhanced image becomes lower in transparence degree and higher in visibility than the wide-field needle-enhanced image in this case, the narrow-field needle-enhanced image is given priority in the puncture support image. The third method can be used in combination with the first method and the second method. For example, after performing weighting according to the second method and assigning transparence degree according to the third method, comparison of luminance degree is performed according to the first method. Then, the part of the puncture needle 12 derived from the narrow-field needle-enhanced image is displayed with lower transparence degree and higher luminance, while the rest of the puncture needle 12 derived from the wide-field needle-enhanced image is displayed with higher transparence degree and lower luminance.

The above-described first to third method can be applied even to the needle-enhanced images that include remainder images of body tissues.

Further, when each of the narrow-field needle-enhanced image and the wide-field needle-enhanced image is such an image that only the puncture needle 12 is extracted as a result of performing gain adjustment on echo signals, the fourth method in which the narrow-field needle-enhanced image is superimposed on the wide-field needle-enhanced image may be used for generating the puncture support image. The fourth method can be combined with any of the above-described first to third methods, and all of those first to fourth methods can be combined with each other.

Those first to fourth methods can be applied to generation of a composite image of a body-tissue image and puncture support image by replacing the narrow-field needle-enhanced image with the body-tissue image and replacing the wide-field needle-enhanced image with the puncture support image.

Additionally, as to a method performed by the image generation function 62 for generating the puncture support image, it is not limited to the first to fourth method, and any method can be applied in which the puncture support image is generated such that the narrow-field needle-enhanced image is given priority over the wide-field needle-enhanced image.

Returning to FIG. 4, after displaying the composite image, the scan control function 61 determines whether ultrasonic scans should be completed or not in the step S10. When it is determined that ultrasonic scans should not be finished, the processing returns to the step S1. Conversely, when it is determined that ultrasonic scans should be finished like a case where a command to complete ultrasonic scans is inputted by a user, the series of procedures is finished.

When the processing returns to the step S1 from the step S10, and when the wide-field needle-enhanced scan was not performed in the last executed procedure of steps S1 to S12, then it is determined as NO in the step 3, and the processing proceeds to the step S11.

Then, in the step S11, the scan control function 61 determines whether or not a predetermined time has elapsed after the completion timing of the wide-field needle-enhanced scan performed last time. Specifically, the scan control function 61 determines whether or not the time-out signal has outputted from the timer 55 to which the timer threshold value Tth was set.

When the predetermined time has not elapsed from the completion timing of the wide-field needle-enhanced scan performed last time (NO at step S11), the processing proceeds to the step S12. Further, even when the wide-field needle-enhanced scan was performed in the last executed procedure of steps S1 to S12 and it is determined as YES in the step S3, the processing proceeds to the step S12 when it was not in the off-plane state in the last wide-field needle-enhanced scan and it is determined as NO in the succeeding step S4. Then, in the step S12, the image generation function 62 generates the puncture support image only from the narrow-field needle-enhanced image generated in the step S2 of this time, and then the processing proceeds to the step S9 in which the image generation function 62 generates a composite image. In this case, execution of the wide-field needle-enhanced scan is omitted. By omitting the wide-field needle-enhanced scan, a frame rate for displaying composite images can be improved.

Meanwhile, when the predetermined time has elapsed after the completion timing of the wide-field needle-enhanced scan performed last time (YES at step S11), the processing proceeds to the step S5 in which the scan control function 61 performs the wide-field needle-enhanced scan. When the predetermined time has elapsed after the completion timing of the wide-field needle-enhanced scan performed last time, the predetermined time has also elapsed after the timing when the off-plane state is resolved. In this case, there is a possibility that the puncture needle 12 is brought to the off-plane state again.

For this reason, when the predetermined time has elapsed from the completion timing of the wide-field needle-enhanced scan performed last time (YES at step S11), for checking whether it is in the off-plane state again or not, the wide-field needle-enhanced scan is performed (step S5), then a puncture support image is generated by combining the narrow-field needle-enhanced image and the wide-field needle-enhanced image (step S6), and then it is determined whether or not it is in the off-plane state (step S7).

When it is determined as the off-plane state in the step S7, a user can immediately recognize that the puncture needle 12 is positionally brought to the off-plane state again with the help of the puncture support information outputted by the notification function 64 in step S6, step S8. That is, a user can immediately recognize that it is brought to the off-plane state, by being notified of information indicative of being in the off-plane state outputted in the form of voice or a displayed image or confirming the puncture needle 12 that is derived from the wide-field needle-enhanced image and is depicted in the composite image.

Conversely, when the off-plane state is still resolved, steps S8 to S10 are executed and the processing returns to the step S1 again. Then, in the subsequent procedure, it is determined as YES in the step S3, and it is determined that it was not in the off-plane state in the step S4 (i.e., it is determined that it was not in the off-plane state in the last wide-field needle-enhanced scan), and then the processing proceeds to the step S12. Thus, when it is determined that the off-plane state is resolved, the frame rate can be recovered immediately from the next composite-image generation processing by omitting the wide-field needle-enhanced scan (step S5).

Although FIG. 4 shows an example of a procedure that includes output of the puncture support image (steps S6 and S12) and notification output of information indicative of being in the off-plane state (step S8) as the puncture support information, either the display output or the notification output may be omitted.

Additionally, in the middle of the procedure of FIG. 4, the ultrasonic diagnostic apparatus 10 may shift to the switching mode in which either one of the narrow-field needle-enhanced image and the wide-field needle-enhanced image is displayed on the display 30, and may return to the processing in FIG. 4 from the switching mode.

Even if the ultrasonic diagnostic apparatus 10 is in the switching mode, for instance, the following procedure can reduce the possibility that a user loses sight of the puncture needle 12. It is assumed that a doctor performs paracentesis while confirming a composite image of a narrow-field needle-enhanced image and a body-tissue image. When it is brought to the off-plane state which makes it difficult to confirm the puncture needle 12 on the composite image, a user can switch images to be displayed on the display 30 from a narrow-field needle-enhanced image to a wide-field needle-enhanced image. For instance, a user can input a command to switch images to be displayed on the display 30 via an input circuit such as a dial, a button, or the like provided on the ultrasonic probe 11. In this manner, a user can easily keep sight of the puncture needle 12 because the puncture needle 12 is reliably depicted in the wide-field needle-enhanced image. Additionally, a user can adjust the position of the ultrasonic probe 11 on the basis of the wide-field needle-enhanced image.

According to at least one of the above-described embodiments, the ultrasonic diagnostic apparatus 10 can assist a user in easily understanding positional relationship between the puncture needle 12 and a biological cross-section corresponding to a body-tissue image.

The processing circuitry 57 in the present embodiment is an example of the processing circuitry recited in the claims.

The term "processor" used in the explanation in the above-described embodiments, for instance, refer to circuitry such as dedicated or general purpose CPUs (Central Processing Units), dedicated or general-purpose GPUs (Graphics Processing Units), or ASICs (Application Specific Integrated Circuits), programmable logic devices including SPLDs (Simple Programmable Logic Devices), CPLDs (Complex Programmable Logic Devices), and FPGAs (Field Programmable Gate Arrays), and the like. The processor implements various types of functions by reading out and executing programs stored in the memory circuitry.

In addition, instead of storing programs in the memory circuitry, the programs may be directly incorporated into the circuitry of the processor. In this case, the processor implements each function by reading out and executing each program incorporated in its own circuitry. Moreover, although in the above-described embodiments an example is shown in which the processing circuitry configured of a single processor implements every function, the processing circuitry may be configured by combining plural processors independent of each other so that each processor implements each function of the processing circuitry by executing corresponding program. When a plurality of processors are provided for the processing circuitry, the memory medium for storing programs may be individually provided for each processor, or one memory circuitry may collectively store programs corresponding to all the functions of the processors.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
a transmission/reception circuit configured to perform a first scan and a second scan, which are different in acoustic field in an elevation direction, by controlling at least one of transducers arranged along an azimuth direction and the elevation direction; and
processing circuitry configured to
generate a first needle-enhanced image by using data acquired in the first scan, and generate a second needle-enhanced image by using data acquired in the second scan, and
wherein the processing circuitry is configured to output voice or an image indicating information to that effect by voice or display when a ratio, which is obtained by dividing a number of pixels of the first needle-enhanced image whose pixel values are equal to or higher than a predetermined pixel value by a number of pixels of the second needle-enhanced image whose pixel values are equal to or higher than the predetermined pixel value, is lower than a predetermined ratio.

2. The ultrasonic diagnostic apparatus according to claim 1,
wherein the processing circuitry is configured to output puncture support information based on the first needle-enhanced image and the second needle-enhanced image, and
wherein the puncture support information includes said voice or image indicating said information output by voice or display.

3. The ultrasonic diagnostic apparatus according to claim 2,
wherein the processing circuitry is configured to generate a puncture support image as the puncture support information by combining the first needle-enhanced image and the second needle-enhanced image.

4. The ultrasonic diagnostic apparatus according to claim 3,
wherein the processing circuitry is configured to generate the puncture support image such that an image of a puncture needle included in the first needle-enhanced image and an image of the puncture needle included in the second needle-enhanced image are different in display mode.

5. The ultrasonic diagnostic apparatus according to claim 4, wherein:
the transmission/reception circuit is configured to perform the first scan and the second scan such that a width of an acoustic field in the elevation direction in the second scan is wider than a width of an acoustic field in the elevation direction in the first scan; and
the processing circuitry is configured to generate the puncture support image so as to give priority to the first needle-enhanced image over the second needle-enhanced image.

6. The ultrasonic diagnostic apparatus according to claim 5,
wherein the processing circuitry is configured to compare for each pixel a luminance value of the first needle-enhanced image and a luminance value of the second needle-enhanced image, and generate the puncture support image such that the larger luminance value is used as a luminance value of corresponding pixel of the puncture support image.

7. The ultrasonic diagnostic apparatus according to claim 5,
wherein the processing circuitry is configured to weight luminance values of at least one of the first needle-enhanced image and the second needle-enhanced image in such that the first needle-enhanced image is given priority over the second needle-enhanced image.

8. The ultrasonic diagnostic apparatus according to claim 5,
wherein the processing circuitry is configured to assign higher transparence degree to the second needle-enhanced image than to the first needle-enhanced image such that the first needle-enhanced image is given priority over the second needle-enhanced image.

9. The ultrasonic diagnostic apparatus according to claim 5,
wherein the processing circuitry is configured to
generate the first needle-enhanced image by extracting only an image data corresponding to a puncture needle from the data acquired in the first scan,
generate the second needle-enhanced image by extracting only an image data corresponding to the puncture needle from the data acquired in the second scan, and
generate the puncture support image such that the first needle-enhanced image is superimposed on the second needle-enhanced image.

10. The ultrasonic diagnostic apparatus according to claim 3,
wherein the processing circuitry is configured to
control the transmission/reception circuit such that the transmission/reception circuit omits execution of the second scan when the ratio, which is obtained by dividing a number of pixels of the first needle-enhanced image whose pixel values are equal to or higher than a predetermined pixel value by a number of pixels of the second needle-enhanced image whose pixel values are equal to or higher than a predetermined pixel value, is not lower than the predetermined ratio, and
generate the puncture support image from the first needle-enhanced image when the execution of the second scan is omitted.

11. The ultrasonic diagnostic apparatus according to claim 10,
wherein the processing circuitry is configured to
control the transmission/reception circuit such that the transmission/reception circuit resumes execution of the second scan when a predetermined time elapses after omission of the execution of the second scan or when an instruction to resume the execution of the second scan is inputted via an input circuit by a user, and
generate the puncture support image by combining the first needle-enhanced image and the second needle-enhanced image when the execution of the second scan is resumed.

12. The ultrasonic diagnostic apparatus according to claim 3, wherein:
the transmission/reception circuit is configured to perform a third scan for generating a body-tissue image of an object; and
the processing circuitry is configured to generate the body-tissue image by using data acquired in the third scan, and generate a composite image of the puncture support image and the body-tissue image.

13. The ultrasonic diagnostic apparatus according to claim 12,
wherein a width of an acoustic field in the elevation direction in the third scan is substantially equal to a narrower one of a width of an acoustic field in the elevation direction in the first scan and a width of an acoustic field in the elevation direction in the second scan.

14. The ultrasonic diagnostic apparatus according to claim 12,
wherein the third scan is a B-mode scan.

15. The ultrasonic diagnostic apparatus according to claim 12,
wherein the processing circuitry is configured to determine pixel values of the body-tissue image and pixel values of the first needle-enhanced image by using a first color map, and determine pixel values of the second needle-enhanced image by using a second color map different from the first color map.

16. The ultrasonic diagnostic apparatus according to claim 1,
wherein the processing circuitry is configured to cause a display to display one of the first needle-enhanced image and the second needle-enhanced image, and switch an image displayed on the display from one of the first needle-enhanced image and the second needle-enhanced image to another in an automatic manner according to setting or in a manual manner according to an instruction from a user.

17. The ultrasonic diagnostic apparatus according to claim 1,
wherein the processing circuitry is configured to cause a display to display a generated image.

18. The ultrasonic diagnostic apparatus according to claim 1, further comprising an ultrasonic probe equipped with plural transducers arranged along the azimuth direction and the elevation direction,
wherein the ultrasonic probe is configured, by being controlled by the processing circuitry, to be capable of generating acoustic fields each of which has a different width in the elevation direction and is symmetric about a center axis along the elevation direction.

19. An ultrasonic image generation method comprising:
performing a first scan and a second scan, which are different in acoustic field in an elevation direction, by controlling at least one of transducers arranged along an azimuth direction and the elevation direction;
generating a first needle-enhanced image by using data acquired in the first scan;
generating a second needle-enhanced image by using data acquired in the second scan;
obtaining a ratio by dividing a number of pixels of the first needle-enhanced image whose pixel values are equal to or higher than a predetermined pixel value by a number of pixels of the second needle-enhanced image whose pixel values are equal to or higher than the predetermined pixel value; and
when the obtained ratio is lower than a predetermined ratio, outputting voice or an image indicating information to that effect by voice or display.

* * * * *